(12) United States Patent
Kitamura et al.

(10) Patent No.: US 9,299,137 B2
(45) Date of Patent: Mar. 29, 2016

(54) IMAGE PROCESSING DEVICE, IMAGE PROCESSING METHOD, AND COMPUTER READABLE STORAGE DEVICE

(75) Inventors: Makoto Kitamura, Hachioji (JP); Yamato Kanda, Hino (JP); Takehiro Matsuda, Hachioji (JP); Takashi Kono, Tachikawa (JP); Masashi Hirota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 50 days.

(21) Appl. No.: 13/617,365

(22) Filed: Sep. 14, 2012

(65) Prior Publication Data
US 2013/0094726 A1    Apr. 18, 2013

(30) Foreign Application Priority Data
Oct. 18, 2011   (JP) .................. 2011-229229

(51) Int. Cl.
*G06K 9/00* (2006.01)
*G06T 7/00* (2006.01)

(52) U.S. Cl.
CPC ..... *G06T 7/0012* (2013.01); *G06T 2207/10024* (2013.01); *G06T 2207/10068* (2013.01); *G06T 2207/30096* (2013.01)

(58) Field of Classification Search
None
See application file for complete search history.

(56) References Cited

U.S. PATENT DOCUMENTS

| 5,815,591 | A * | 9/1998 | Roehrig et al. | 382/130 |
| 6,112,112 | A * | 8/2000 | Gilhuijs et al. | 600/425 |
| 6,246,782 | B1 * | 6/2001 | Shapiro et al. | 382/128 |
| 8,086,002 | B2 * | 12/2011 | Zhang et al. | 382/128 |
| 2003/0031354 | A1 * | 2/2003 | Takeo | 382/132 |
| 2003/0099391 | A1 * | 5/2003 | Bansal et al. | 382/131 |
| 2004/0264749 | A1 * | 12/2004 | Skladnev et al. | 382/128 |
| 2004/0267102 | A1 * | 12/2004 | Skladnev et al. | 600/315 |
| 2005/0259856 | A1 * | 11/2005 | Dehmeshki | 382/131 |
| 2006/0241463 | A1 * | 10/2006 | Shau et al. | 600/455 |

(Continued)

FOREIGN PATENT DOCUMENTS

| JP | 2005-192880 A | 7/2005 |
| JP | 2009-77800 A | 4/2009 |
| JP | 2010-115260 A | 5/2010 |

OTHER PUBLICATIONS

Maitra et al. "Automated digital Mammogram Segmentation for Detection of Abnormal Masses Using Binary Momgeneity Enhancement Algorithm" IJCSE, vol. 2 No. 3 Jun.-Jul. 2011.*

(Continued)

*Primary Examiner* — Bhavesh Mehta
*Assistant Examiner* — Oneal R Mistry
(74) *Attorney, Agent, or Firm* — Scully, Scott, Murphy & Presser, P.C.

(57) ABSTRACT

An image processing device includes: a candidate abnormal region determining unit that determines a candidate abnormal region from an image using a first determination criterion; a bubble region determining unit that determines a bubble region from the image; a bubble inside determining unit that determines whether the candidate abnormal region is present inside the bubble region based on a determination result of the bubble region; and an abnormal region determining unit that determines whether the candidate abnormal region is an abnormal region using a second determination criterion different from the first determination criterion when the candidate abnormal region is determined to be present inside the bubble region.

19 Claims, 13 Drawing Sheets

(56) References Cited

U.S. PATENT DOCUMENTS

| | | | |
|---|---|---|---|
| 2008/0021502 A1* | 1/2008 | Imielinska | A61B 6/032 607/1 |
| 2009/0148014 A1 | 6/2009 | Kanda | |
| 2011/0026798 A1* | 2/2011 | Madabhushi et al. | 382/131 |
| 2012/0033861 A1* | 2/2012 | Dai et al. | 382/128 |

OTHER PUBLICATIONS

Japanese Office Action dated Jun. 30, 2015 issued in corresponding Japanese Patent Application No. 2011-229229.

* cited by examiner

IMAGE PROCESSING DEVICE, IMAGE PROCESSING METHOD, AND COMPUTER READABLE STORAGE DEVICE

CROSS-REFERENCE TO RELATED APPLICATIONS

This application is based upon and claims the benefit of priority from Japanese Patent Application No. 2011-229229, filed on Oct. 18, 2011, the entire contents of which are incorporated herein by reference.

BACKGROUND OF THE INVENTION

1. Field of the Invention

The present invention relates to an image processing device, an image processing method, and a computer readable storage device for determining an abnormal region from an image obtained by imaging a lumen of a living body.

2. Description of the Related Art

In the related art, as image processing on images (hereinafter referred to as intra-luminal images or simply as images) obtained by imaging the lumen of a living body using a medical observation device such as an endoscope or a capsule endoscope, a technique of detecting an abnormal region based on hue information of the image is disclosed in Japanese Laid-open Patent Publication No. 2005-192880. More specifically, in Japanese Laid-open Patent Publication No. 2005-192880, the pixel value of each pixel or a mean pixel value thereof is mapped onto a feature space based on the color feature data, a normal mucosal cluster and an abnormal cluster are specified after performing clustering in the feature space, and a pixel region belonging to the abnormal cluster is detected as an abnormal region.

SUMMARY OF THE INVENTION

An image processing device according to an aspect of the invention includes: a candidate abnormal region determining unit that determines a candidate abnormal region from an image using a first determination criterion; a bubble region determining unit that determines a bubble region from the image; a bubble inside determining unit that determines whether the candidate abnormal region is present inside the bubble region based on a determination result of the bubble region; and an abnormal region determining unit that determines whether the candidate abnormal region is an abnormal region using a second determination criterion different from the first determination criterion when the candidate abnormal region is determined to be present inside the bubble region.

An image processing method according to another aspect of the invention includes: determining a candidate abnormal region from an image using a first determination criterion; determining a bubble region from the image; determining whether the candidate abnormal region is present inside the bubble region based on the determination result of the bubble region; and determining whether the candidate abnormal region is an abnormal region using a second determination criterion different from the first determination criterion when the candidate abnormal region is determined to be present inside the bubble region.

A computer readable storage device according to still another aspect of the invention has an executable program stored thereon, wherein the program instructs a processor to perform: determining a candidate abnormal region from an image using a first determination criterion; determining a bubble region from the image; determining whether the candidate abnormal region is present inside the bubble region based on the determination result of the bubble region; and determining whether the candidate abnormal region is an abnormal region using a second determination criterion different from the first determination criterion when the candidate abnormal region is determined to be present inside the bubble region.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
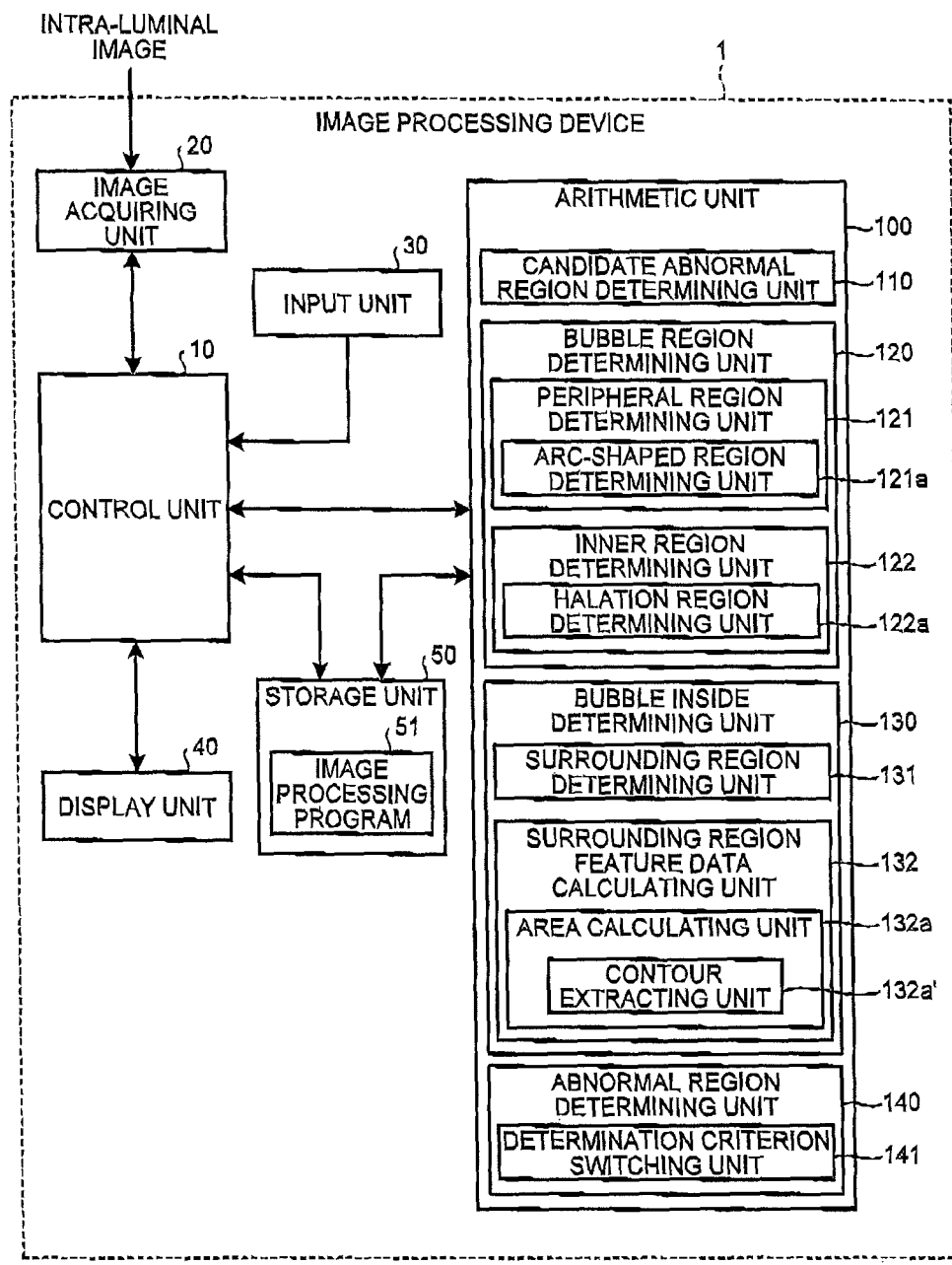
FIG. 1 is a block diagram illustrating the configuration of an image processing device according to a first embodiment of the invention.

Hereinafter an image processing device, an image processing method, and an image processing program according to embodiments of the invention will be explained with reference to the drawings. The invention is not limited to these embodiments. In the respective drawings, the same portions are denoted by the same reference numerals.

In the following embodiments, as an example, a process on a series of intra-luminal images (hereinafter simply referred to as images) obtained by imaging the lumen of a subject in a time-sequential order using a medical observation device such as an endoscope or a capsule endoscope will be explained. In the following description, the images subjected to image processing are color images which have 256 pixel levels (pixel values) for each of the respective color components of R (red), G (green), and B (blue) at the respective pixel positions, for example. The invention is not limited to intra-luminal images but can be widely applied to a case of extracting a specific region from images acquired using other general image acquisition devices.

First Embodiment

FIG. 1 is a block diagram illustrating the configuration of an image processing device according to a first embodiment of the invention. An image processing device 1 illustrated in FIG. 1 includes a control unit 10 that controls the operation of the entire image processing device 1, an image acquiring unit 20 that acquires image data corresponding to an image captured by a medical observation device, an input unit 30 that receives input signals input from an external device, a display unit 40 that displays various screens, a storage unit 50 that stores the image data acquired by the image acquiring unit 20 and various programs, and a arithmetic unit 100 that executes predetermined image processing on the image data.

The control unit 10 is implemented by hardware such as a CPU. The control unit 10 reads various programs stored in the storage unit 50 to thereby transmit instructions and data to the respective units of the image processing device 1 in accordance with the image data input from the image acquiring unit 20 or an operation signal input from the input unit 30 and control the operation of the entire image processing device 1 in an integrated manner.

The image acquiring unit 20 is appropriately configured according to an aspect of a system that includes the medical observation device. For example, when the medical observation device is a capsule endoscope, and a portable recording medium is used in exchanging of image data with the medical observation device, the image acquiring unit 20 is configured as a reader device that detachably attaches the recording medium and reads image data of the intra-luminal images stored in the recording medium. Moreover, when a server that stores image data of the intra-luminal images captured by the medical observation device is provided, the image acquiring unit 20 is configured as a communication device that is connected to the server and performs data communication with the server to acquire the image data of the intra-luminal images. Alternatively, the image acquiring unit 20 may be configured as an interface device or the like that receives image signals from the medical observation device via a cable.

The input unit 30 is implemented as an input device such as, for example, a keyboard, a mouse, a touch panel, or various switches, and outputs received input signals to the control unit 10.

The display unit 40 is implemented as a display device such as an LCD or an EL display, and displays various screens including intra-luminal images under control of the control unit 10.

The storage unit 50 is implemented as various IC memories called a ROM or a RAM such as a rewritable flash memory, an internal hard disk or a hard disk connected to a data communication terminal, or an information storage medium such as a CD-ROM, and a reading device thereof. The storage unit 50 stores a program for causing the image processing device 1 to operate and causing the image processing device 1 to execute various functions, and data or the like used during the execution of the program in addition to the image data of the intra-luminal images acquired by the image acquiring unit 20. Specifically, the storage unit 50 stores an image processing program 51 for executing a process of determining a candidate abnormal region from an image using a first predetermined criterion, determining a bubble region, and determining whether the candidate abnormal region is an abnormal region using a second criterion when it is determined that the candidate abnormal region is present within the bubble region. The storage unit 50 also stores various determination criteria used during the execution of the image processing program 51.

The arithmetic unit 100 is implemented by hardware such as a CPU. The arithmetic unit 100 performs image processing on the image data corresponding to the intra-luminal image by reading the image processing program 51 and performs various arithmetic processes for determining an abnormal region from an intra-luminal image.

Next, a detailed configuration of the arithmetic unit 100 will be explained.

As illustrated in FIG. 1, the arithmetic unit 100 includes a candidate abnormal region determining unit 110 that determines a candidate abnormal region from an image using a first determination criterion, a bubble region determining unit 120 that determines a bubble region from the image, a bubble inside determining unit 130 that determines whether the candidate abnormal region is present inside the bubble region based on the determination result of the bubble region, and an abnormal region determining unit 140 that determines whether the candidate abnormal region is an abnormal region using a second determination criterion different from the first determination criterion when the candidate abnormal region is determined to be present inside the bubble region.

The bubble region determining unit 120 includes a peripheral region determining unit 121 that determines a region having the features of the peripheral region of the bubble region and an inner region determining unit 122 that determines a region having the features of the inner region of the bubble region. The peripheral region determining unit 121 includes an arc-shaped region determining unit 121a that determines an arc-shaped region which is the feature of the peripheral region of the bubble region. Moreover, the inner region determining unit 122 includes a halation region determining unit 122a that determines a halation region which is the feature of the inner region of the bubble region.

The bubble inside determining unit 130 includes a surrounding region determining unit 131 that determines a surrounding region of the candidate abnormal region and a surrounding region feature data calculating unit 132 that calculates the feature data of the surrounding region based on the determination result of the bubble region in the surrounding region and a region in the vicinity of the surrounding region. The surrounding region feature data calculating unit 132 includes an area calculating unit 132a that calculates the area of the bubble region in the surrounding region and the region in the vicinity of the surrounding region. More specifically, the area calculating unit 132a includes a contour extracting unit 132a' that extracts contour pixels of the surrounding region.

The abnormal region determining unit 140 includes a determination criterion switching unit 141 that switches the determination Criterion based on whether the surrounding region of the candidate abnormal region is present inside the bubble region.

Figure 2:
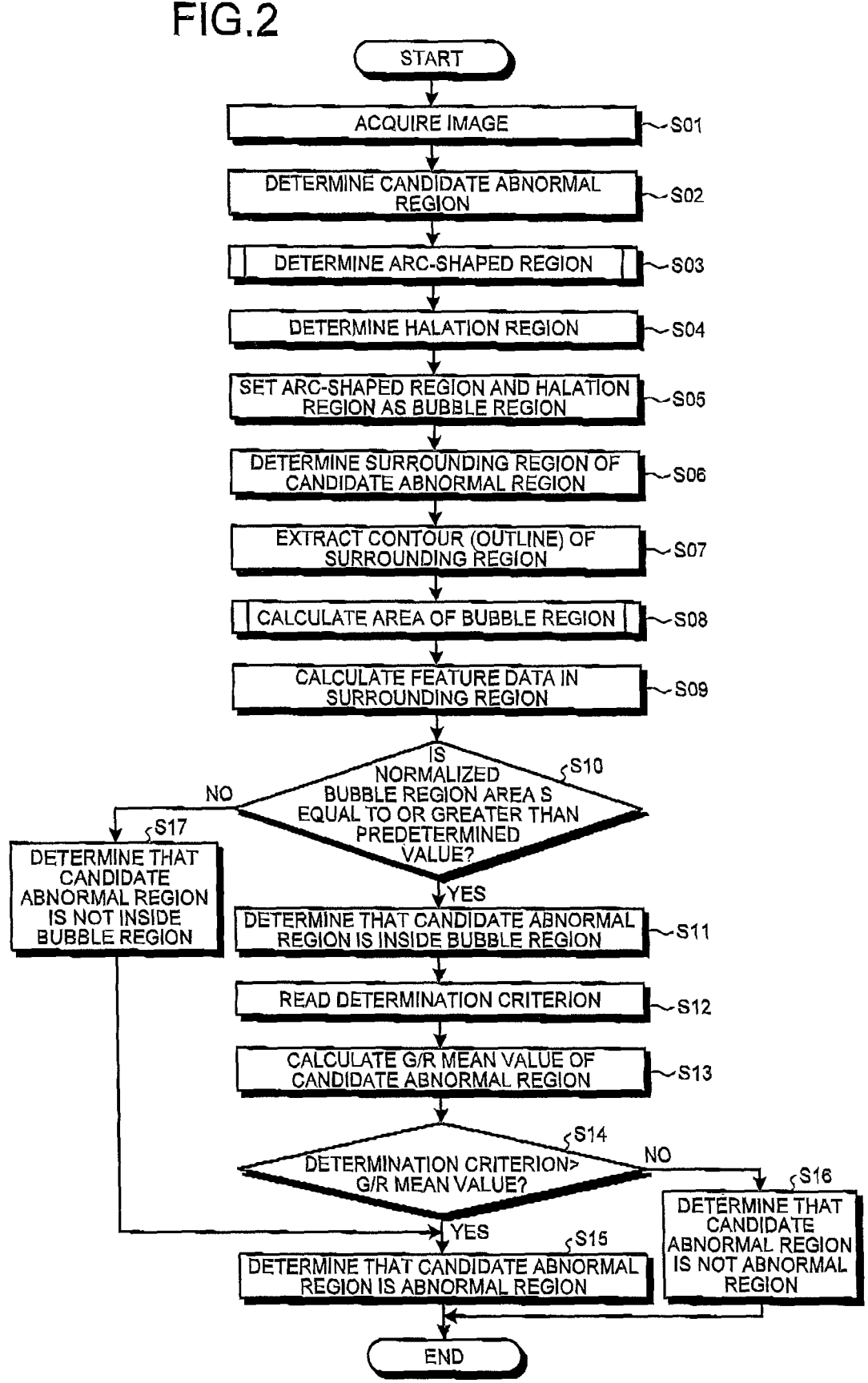
FIG. 2 is a flowchart illustrating the operation of the image processing device illustrated in FIG. 1.

Next, the operation of the image processing device 1 will be explained. FIG. 2 is a flowchart illustrating the operation of the image processing device 1.

Figure 3:
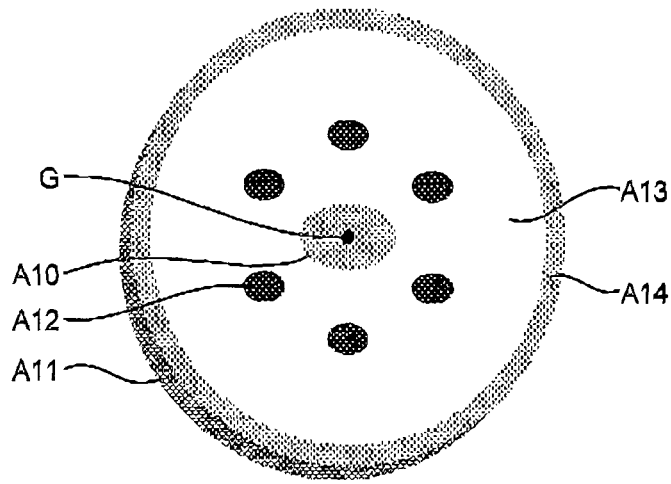
FIG. 3 is a schematic view illustrating a part of a processing target image as an example.

First, in step S01, the image acquiring unit 20 acquires a series of intra-luminal images obtained by imaging the lumen of a subject and stores the intra-luminal images in the storage unit 50. The arithmetic unit 100 sequentially reads image data corresponding to a processing target image from the storage unit 50. FIG. 3 is a schematic view illustrating a part of the processing target image read by the arithmetic unit 100 as an example.

Subsequently, in step S02, the candidate abnormal region determining unit 110 determines a candidate abnormal region based on the color feature data of the image. More specifically, the candidate abnormal region determining unit 110 calculates a G/R value from the pixel values of the respective pixels that constitute an image and determines a region in which the G/R value is smaller than a predetermined determination criterion value as a candidate abnormal region A10. That is, a region in which red colors are relatively strong (a region in which bleeding or reddening is suspicious) is extracted from the image as the candidate abnormal region A10.

In step S03, the peripheral region determining unit 121 (the arc-shaped region determining unit 121a) determines an arc-shaped region in the image. Although various methods can be used as a method of determining the arc-shaped region, in the first embodiment, a method disclosed in Japanese Laid-open Patent Publication No. 2007-313119 is used.

Figure 4:
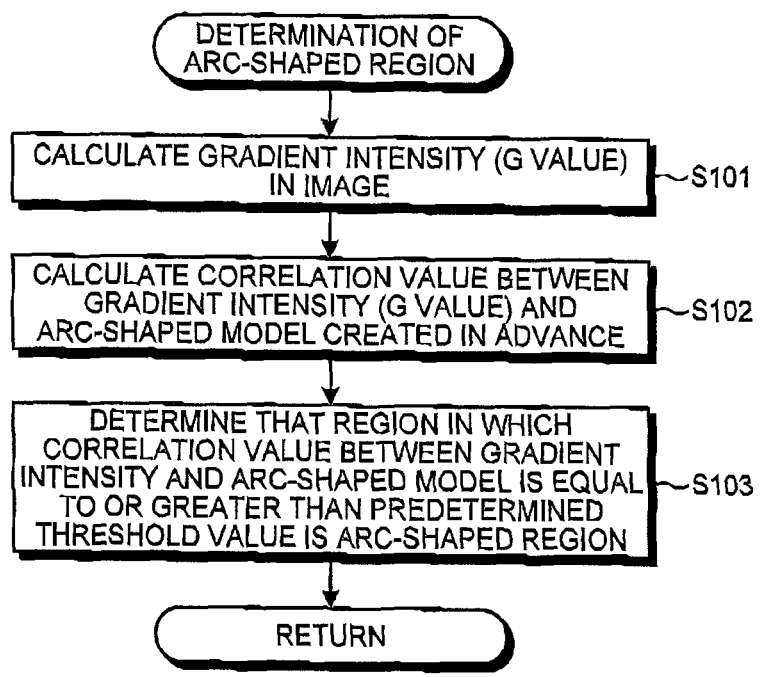
FIG. 4 is a flowchart illustrating a detailed process of determining an arc-shaped region.

FIG. 4 is a flowchart illustrating a detailed process of step S03. First, in step S101, the arc-shaped region determining unit 121a calculates a gradient intensity (G value) in the image. Subsequently, in step S102, a correlation value between the gradient intensity (G value) and an arc-shaped model created in advance is calculated. Further, in step S103, a region in which the correlation value between the gradient intensity and the arc-shaped model is equal to or greater than a predetermined threshold value is determined as an arc-shaped region A11 (see FIG. 3). After that, the processing returns to a main routine.

In step S04, the inner region determining unit 122 (the halation region determining unit 122a) determines a halation region in the image. Specifically, a luminance value Y is calculated from the pixel values (RGB values) of the respective pixels using the following equation (1) (see Digital Image Processing, CG-ARTS Society, p. 299). Moreover, a region in which the luminance value Y is equal to or greater than a predetermined threshold value is determined as a halation region A12 (see FIG. 3).

$$Y=0.3 \times R+0.59 \times G+0.11 \times B \quad (1)$$

In step S05, the bubble region determining unit 120 sets the arc-shaped region A11 determined by the peripheral region determining unit 121 and the halation region A12 determined by the inner region determining unit 122 as the bubble region. In many cases, the bubble region includes both the arc-shaped region A11 and the halation region A12.

Figure 5:
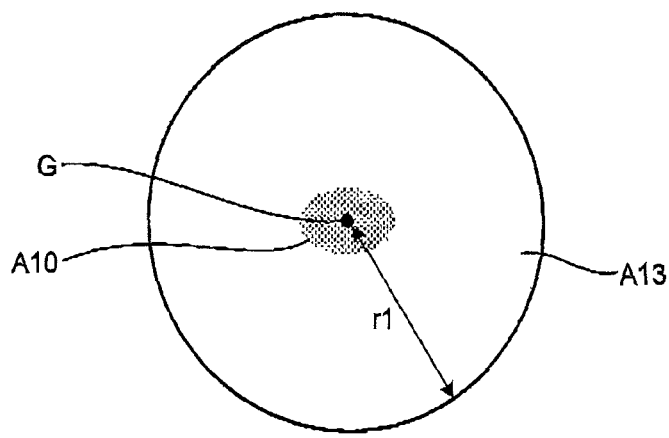
FIG. 5 is a diagram explaining a method of determining a surrounding region of a candidate abnormal region.

In step S06, the surrounding region determining unit 131 determines the surrounding region of the candidate abnormal region A10. More specifically, first, the surrounding region determining unit 131 calculates the gravity center position G of the candidate abnormal region A10 in the image as illustrated in FIG. 5. Moreover, a region included in a circle of which the origin is located at the gravity center position G and which has a radius of r1 is extracted as a surrounding region A13. The value of the radius r1 may be a predetermined value or may be determined adaptively based on the area of the candidate abnormal region A10.

In step S07, the contour extracting unit 132a' executes a contour tracking process (see Digital Image Processing, CG-ARTS Society, p. 178) to extract a contour (outline) region A14 of the surrounding region A13.

In step S08, the area calculating unit 132a calculates the area of the bubble region in the surrounding region A13 and a region in the vicinity of the surrounding region A13. For example, in the case of FIG. 3, the bubble region (the halation region) A12 is present in the surrounding region A13, and the bubble region (the arc-shaped region) A11 is present so as to overlap the contour region A14 of the surrounding region A13. The area calculating unit 132a calculates the total areas of the bubble regions A11 and A12.

Figure 6:
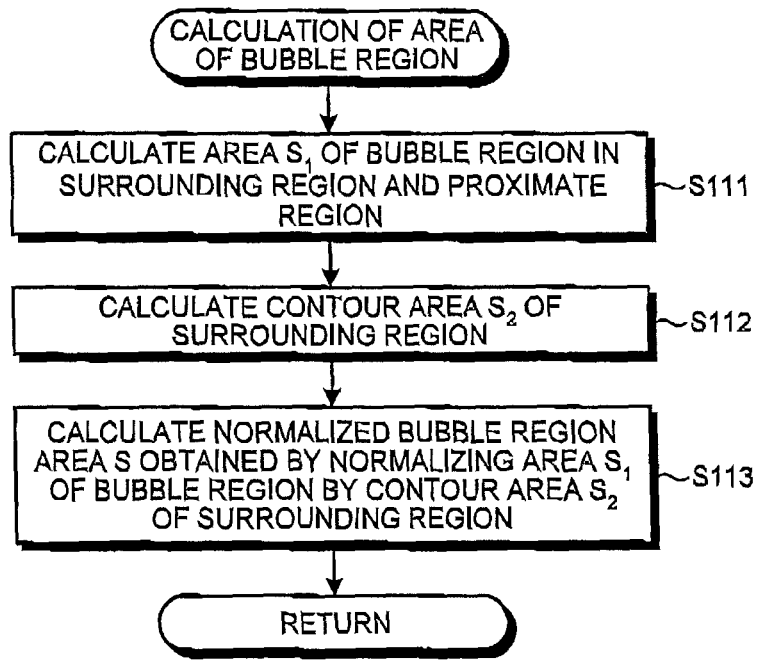
FIG. 6 is a flowchart illustrating a detailed process of calculating the area of a bubble region in a surrounding region and a region in the vicinity of the surrounding region.

FIG. 6 is a flowchart illustrating a detailed process of step S08. In step S111, first, the area calculating unit 132a calculates the total area $S_1$ of the bubble regions A11 and A12 in the surrounding region A13 and the region in the vicinity of the surrounding region A13. Subsequently, in step S112, the area $S_2$ of a contour region (outline) A14 of the surrounding region A13 is calculated. Further, in step S113, the area $S_1$ of the bubble region is normalized by the area $S_2$ of the contour region A14 of the surrounding region using the following equation (2) to calculate a normalized bubble region area S.

$$S=S_1/S_2 \quad (2)$$

In the above equation (2), the area $S_1$ may be divided by the area of the surrounding region A13 instead of the area $S_2$ of the contour region A14, or the area $S_1$ may be divided by the sum of the areas of the surrounding region A13 and the contour region A14.

After that, the processing returns to the main routine.

In step S09, the surrounding region feature data calculating unit 132 uses the normalized bubble region area S as the feature data of the surrounding region A13. Incidentally, the value itself of the area $S_1$ of the bubble regions A11 and A12 or the determination result (1 for present and 0 for absent) on the presence of a bubble region in the surrounding region A13 and a region in the vicinity of the surrounding region A13 may be used as the feature data of the surrounding region A13.

In step S10, the bubble inside determining unit 130 determines whether the normalized bubble region area S in the surrounding region A13 of the candidate abnormal region A10 is equal to or greater than a predetermined threshold value (predetermined value). When the normalized bubble region area S is equal to or greater than the predetermined value (Yes in step S10), the bubble inside determining unit 130 determines that the candidate abnormal region A10 is inside the bubble region (step S11). This is because the greater the area of the region having the features of the bubble region in the surrounding region A13 and a region in the vicinity of the surrounding region A13 is, the higher the possibility of the candidate abnormal region A10 being an inner region of the bubble region is. When the area $S_1$ of the bubble regions A11 and A12 or the presence of the bubble region in the surrounding region A13 and the region in the vicinity of the surrounding region A13 is used as the feature data of the surrounding region A13, the candidate abnormal region A10 may be determined to be present inside the bubble region when the area $S_1$ is equal to or greater than a predetermined value or the bubble region is determined to be present.

Subsequently, in step S12, the determination criterion switching unit 141 reads a determination criterion value created in advance from the storage unit 50. The criterion value read at this time is smaller than the criterion value used by the candidate abnormal region determining unit 110 in step S02.

That is, the region (the abnormal region) which is determined to fall within the range defined by the criterion value read in step S12 is fewer than the region (the candidate abnormal region) which is determined to fall within the range defined by the criterion value in step S02. In other words, the criterion value read in step S12 is stricter than the criterion value used in step S02.

In steps S13 to S15, the abnormal region determining unit 140 determines whether the candidate abnormal region A10 is an abnormal region based on the determination criterion read in step S12. Specifically, first, in step S13, the abnormal region, determining unit 140 calculates a mean value (G/R mean value) of the G/R value of the candidate abnormal region A10. Subsequently, in step S14, the abnormal region determining unit 140 determines whether the calculated G/R mean value is smaller than a determination criterion. When the G/R mean value is determined to be smaller than the determination criterion (Yes in step S14), the abnormal region determining unit 140 determines that the candidate abnormal region A10 is an abnormal region such as a bleeding region or a reddening region (step S15). In this case, a region in which the red colors are stronger than the determination result in step S02 is determined as an abnormal region.

On the other hand, when the G/R mean value is equal to or greater than the determination criterion (No in step 314), the abnormal region determining unit 140 determines that the candidate abnormal region A10 is not an abnormal region (step S16).

Moreover, in step S10, when the normalized bubble region area S is determined to be smaller than a predetermined value (No in step S10), the candidate abnormal region A10 is determined not to be present inside the bubble region (step S17). In this case, the candidate abnormal region A10 is determined as an abnormal region according to the determination in step S02 (step S15).

As described above, according to the first embodiment, when a candidate abnormal region, which is determined based on a predetermined criterion value from an image, is determined to be present inside a bubble region, it is determined whether the candidate abnormal region is an abnormal region in accordance with a different criterion value such that the corresponding regions are fewer than that obtained when the predetermined criterion value is used. Therefore, it is possible to suppress a mucosal region inside bubbles from being erroneously detected as an abnormal region.

First Modification Example

In the first embodiment described above, the G/R value and the luminance value Y have been calculated for each pixel, and the candidate abnormal region and the halation region have been determined. However, an image may be divided into small regions, and the candidate abnormal region and the halation region may be determined for each small region. In this case, a mean value in each small region of the G/R value and the luminance value Y of the respective pixels is used for the determination process.

A process of dividing an image based on edge intensity is performed as follows. First, the edge intensity of each of the respective pixels included in a processing target image is calculated. In calculating the edge intensity, a known method such as a differential filtering process using the Sobel filter may be used. Subsequently, the image is divided into multiple edge regions using the ridges of the edge intensities as boundaries. More specifically, an edge intensity image which uses the respective pixels edge intensities as pixel values is created, and a gradient direction of the edge intensities in the pixels of the edge intensity image is acquired. In this case, the gradient direction is set in a direction where the value of the edge intensity decreases. Moreover, pixels having the minimum value which the respective pixels reach when moving along the gradient direction are searched, and the image is divided so that the pixels at the starting point which have reached the adjacent pixels having the minimum value are included in the same region (see WO 2006/080239 A).

As another image division method, an existing method such as a watershed algorithm can be also used (see Luc Vincent and Pierre Soille, "Watersheds in digital spaces: An efficient algorithm based on immersion simulations", IEEE Transactions on Pattern Analysis and Machine Intelligence, Vol. 13, No. 6, pp. 583-598, June 1991).

According to the first modification example, since the candidate abnormal region and the halation region are determined based on the feature data of each of the small regions including multiple pixels, it is possible to perform the determination process by reflecting the features of each small region and to improve the computation speed.

Second Modification Example

In the first embodiment, it is determined whether the candidate abnormal region is inside the bubble region using the value obtained by normalizing the total area of the bubble region (the halation region) present in the surrounding region of the candidate abnormal region and the bubble region (the arc-shaped region) near the contour region of the surrounding region by the area of the contour region as the feature data. However, it is not always necessary to extract the contour region of the surrounding region. For example, the determination may be performed using the total area of the halation region and the arc-shaped region present in the surrounding region and the region in the vicinity of the surrounding region or a value obtained by normalizing the total area by the area of the surrounding region as the feature data. Alternatively, the determination may be performed based on whether a predetermined amount of the arc-shaped region is present in the surrounding region and the region in the vicinity of the surrounding region (for example, the total area of the arc-shaped region or the sum of the lengths of the arcs is equal to or greater than a predetermined threshold value).

Second Embodiment

Next, a second embodiment of the invention will be explained.

Figure 7:
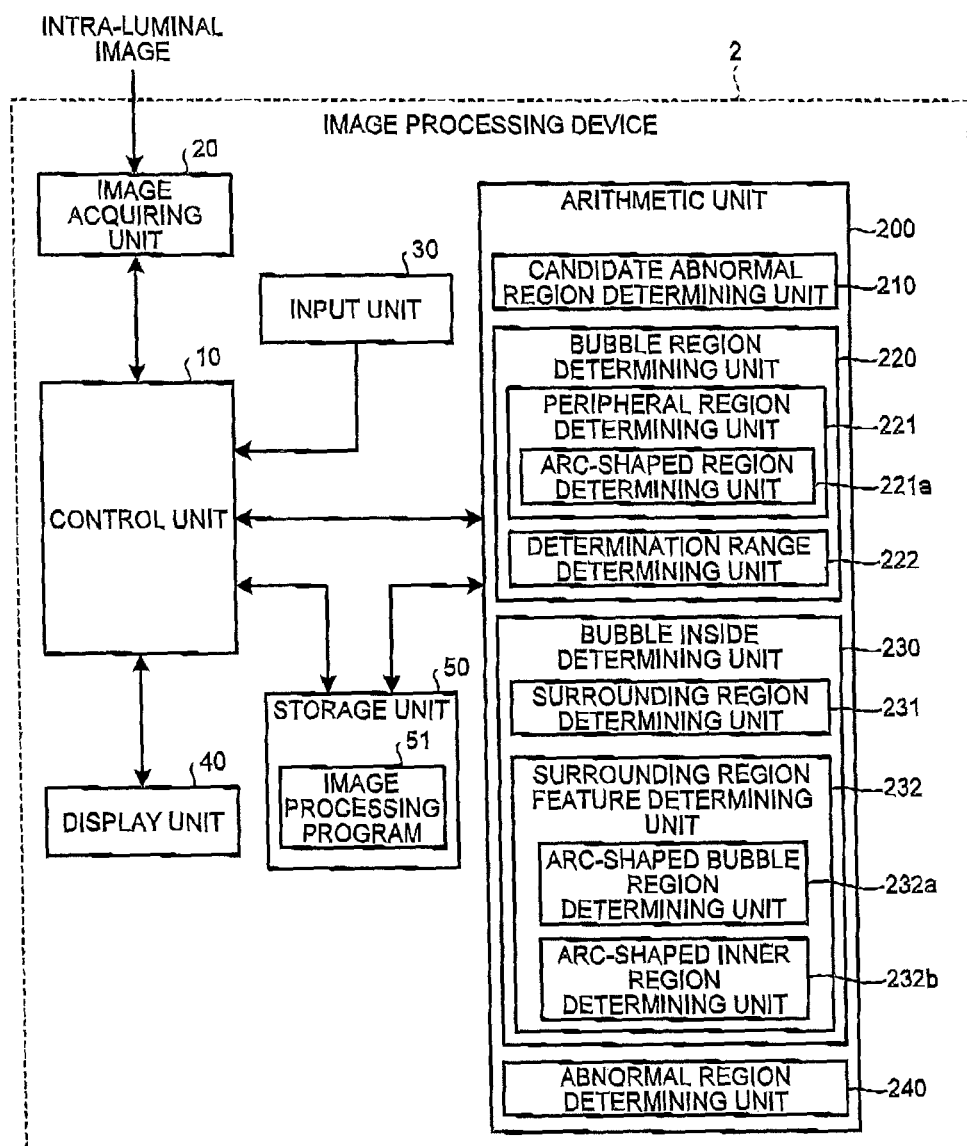
FIG. 7 is a block diagram illustrating the configuration of an image processing device according to a second embodiment of the invention.

FIG. 7 is a block diagram illustrating the configuration of an image processing device according to the second embodiment. As illustrated in FIG. 7, an image processing device 2 according to the second embodiment includes an arithmetic unit 200 which includes a candidate abnormal region determining unit 210 that determines a candidate abnormal region from an image, a bubble region determining unit 220 that determines a bubble region from the image, a bubble inside determining unit 230 that determines whether the candidate abnormal region is present inside the bubble region based on the determination result of the bubble region, and an abnormal region determining unit 240 that determines whether the candidate abnormal region is an abnormal region. The configuration of the image processing device 2 other than the arithmetic unit 200 is the same as that illustrated in FIG. 1.

The bubble region determining unit 220 includes a peripheral region determining unit 221 that determines a region having the features of the peripheral region of the bubble region and a determination range determining unit 222 that determines a determination range where the bubble region in the image is determined based on the determination result of the candidate abnormal region. The peripheral region determining unit 221 includes an arc-shaped region determining unit 221a that determines an arc-shaped region.

The bubble inside determining unit 230 includes a surrounding region determining unit 231 that determines the surrounding region of the candidate abnormal region and a surrounding region feature determining unit 232 that determines the features of the bubble region in the surrounding region based on the determination result of the bubble region in the surrounding region and the region in the vicinity of the surrounding region.

More specifically, the surrounding region feature determining unit 232 includes an arc-shaped bubble region determining unit 232a that determines whether the bubble region in the surrounding region and the region in the vicinity of the surrounding region includes an arc-shaped region and an arc-shaped inner region determining unit 232b that determines whether the surrounding region is an inner region of the arc-shaped region.

Figure 8:
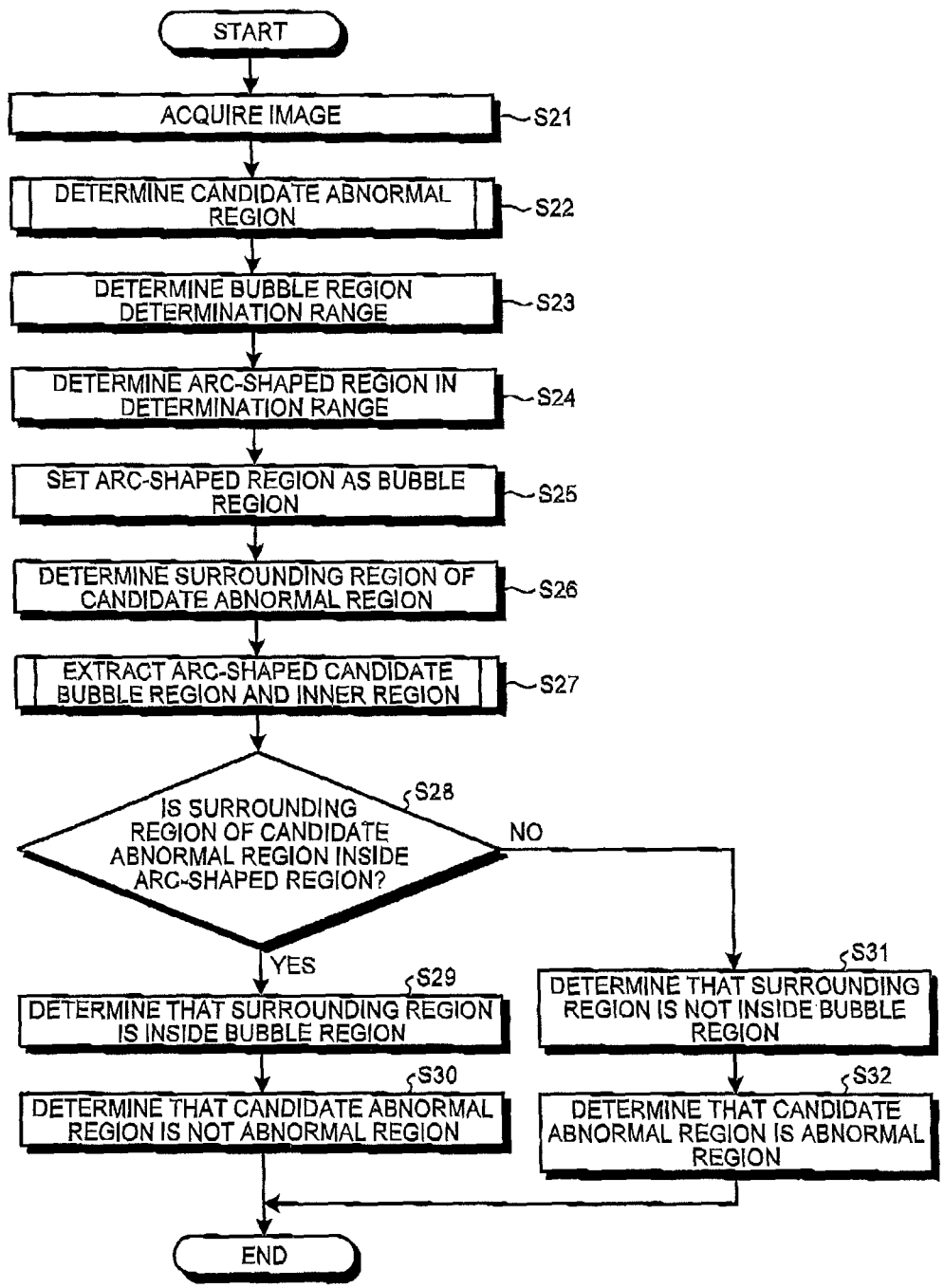
FIG. 8 is a flowchart illustrating the operation of the image processing device according to the second embodiment of the invention.

Next, the operation of the image processing device according to the second embodiment will be explained. FIG. 8 is a flowchart illustrating the operation of the image processing device according to the second embodiment.

First, in step S21, the arithmetic unit 200 acquires image data corresponding to a processing target image. The detailed process of step S21 is the same as that of step S01 of the first embodiment.

Subsequently, in step S22, the candidate abnormal region determining unit 210 determines a candidate abnormal region based on a color feature data.

Figure 9:
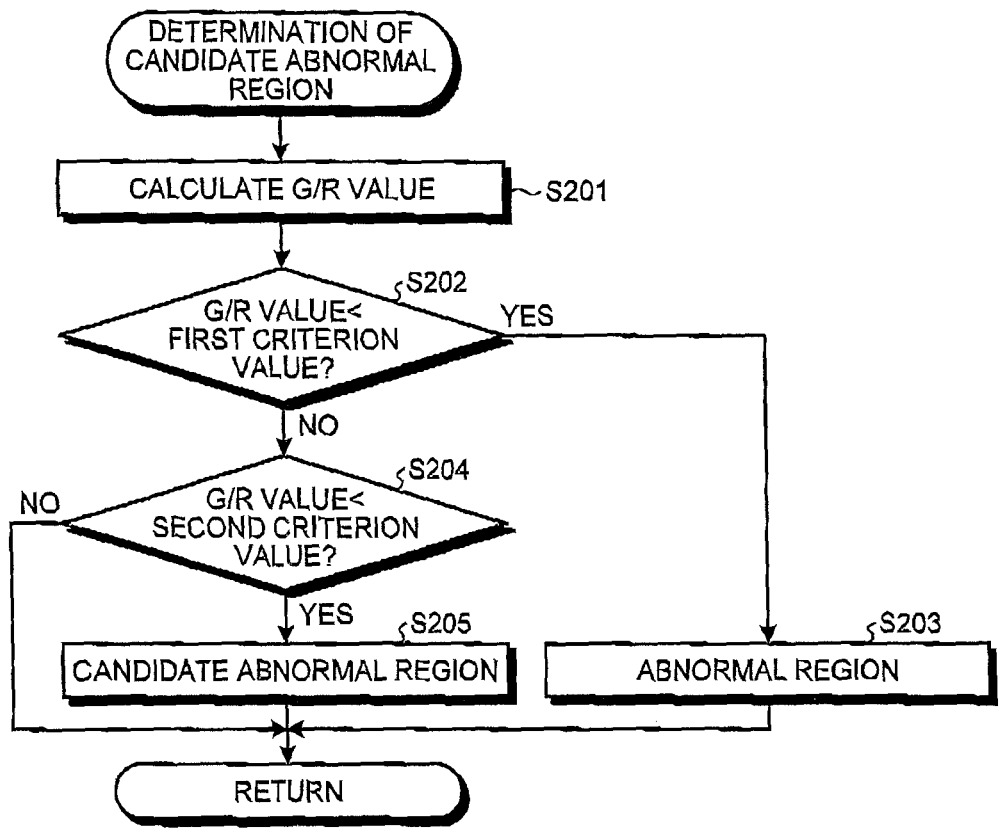
FIG. 9 is a flowchart illustrating a detailed process of determining a candidate abnormal region.

FIG. 9 is a flowchart illustrating a detailed process of determining the candidate abnormal region. In step S201, the candidate abnormal region determining unit 210 calculates the G/R value from the pixel values of the respective pixels that constitute the image. In this case, similarly to the first modification example, the mean value of the G/R values may be calculated for each of the small regions that are obtained by dividing the image.

In step S202, the candidate abnormal region determining unit 210 determines whether each of the calculated G/R values is smaller than a first criterion value set in advance. When a region in which the G/R value is smaller than the first criterion value is detected (Yes in step S202), the region is determined as an abnormal region such as a bleeding region or a reddening region (step S203).

On the other hand, with respect to the region in which the G/R value is equal to or greater than the first criterion value (No in step S202), the candidate abnormal region determining unit 210 determines whether the G/R value in the region is smaller than a second criterion value set in advance (second criterion value>first criterion value) (step S204). When the region in which the G/R value is smaller than the second criterion value is detected (Yes in step S204), the region is determined as a candidate abnormal region which is likely to be an abnormal region but with low confidence (step S205). The region in which the G/R value is equal to or greater than the second criterion value (No in step S204) is determined neither as an abnormal region nor a candidate abnormal region. After that, the processing returns to the main routine.

Figure 10:
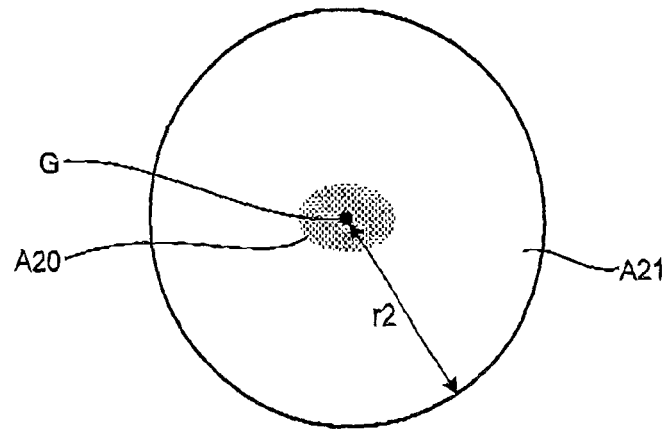
FIG. 10 is a diagram explaining a method of determining a bubble region determination range.

In step S23, the determination range determining unit 222 determines a determination range where the bubble region in the image is determined. Specifically, as illustrated in FIG. 10, the gravity center position G of a candidate abnormal region A20 determined from the image is calculated, and a region included in a circle of which the origin is located at the gravity center position G and which has a radius of r2 is determined as a determination range A21. The value of the radius r2 may be a predetermined value set in advance and may be determined adaptively based on the area of the candidate abnormal region A20.

Figure 11:
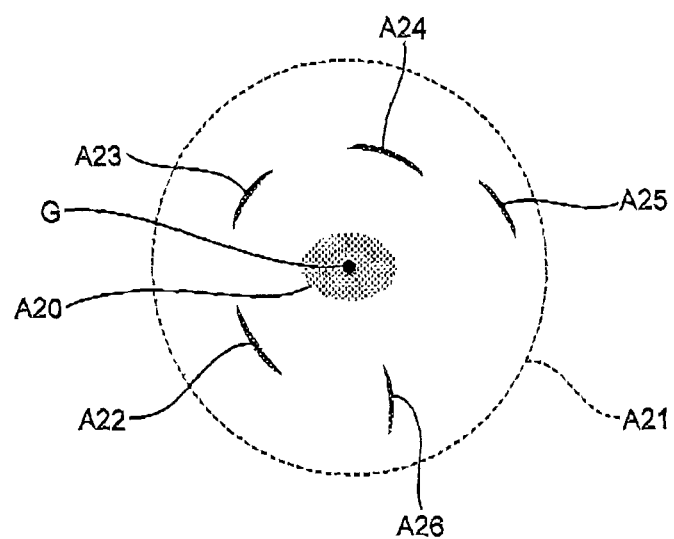
FIG. 11 is a schematic view illustrating an arc-shaped region determined from the determination range.

In step S24, the peripheral region determining unit 221 (the arc-shaped region determining unit 221a) determines an arc-shaped region in the determination range A21. A detailed process of a method of determining the arc-shaped region is the same as that described with reference to FIG. 4 in step S03 of the first embodiment. FIG. 11 illustrates an example of arc-shaped regions A22 to A26 determined in this way.

In step S25, the bubble region determining unit 220 sets the arc-shaped regions A22 to A26 determined in step S24 as candidate bubble regions.

Figure 12:
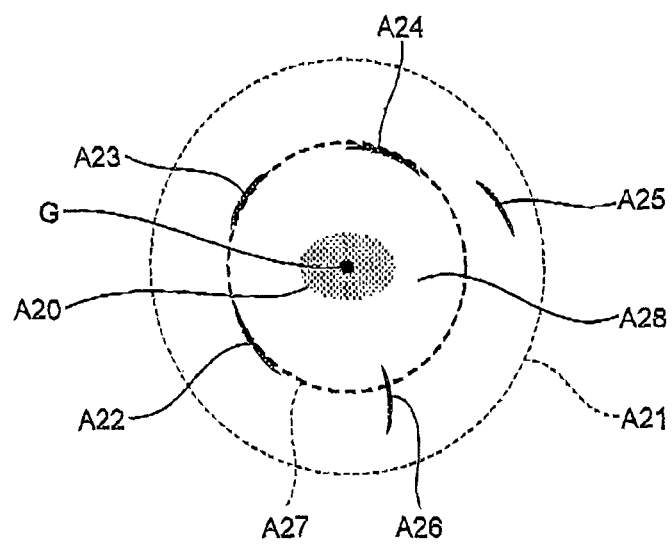
FIG. 12 is a diagram explaining a method of determining a candidate bubble region.

In step S26, the surrounding region determining unit 231 determines the surrounding region of the candidate abnormal region A20. A detailed process of step S26 is the same as that described in step S06 of the first embodiment. FIG. 12 illustrates a surrounding region A27 determined in step S26.

In step S27, the arc-shaped bubble region determining unit 232a extracts an arc-shaped candidate bubble region from the candidate bubble regions (arc-shaped regions) A22 to A26 in the surrounding region A27 of the candidate abnormal region A20 and a region in the vicinity of the surrounding region A27 and extracts an arc-shaped inner region.

Figure 13:
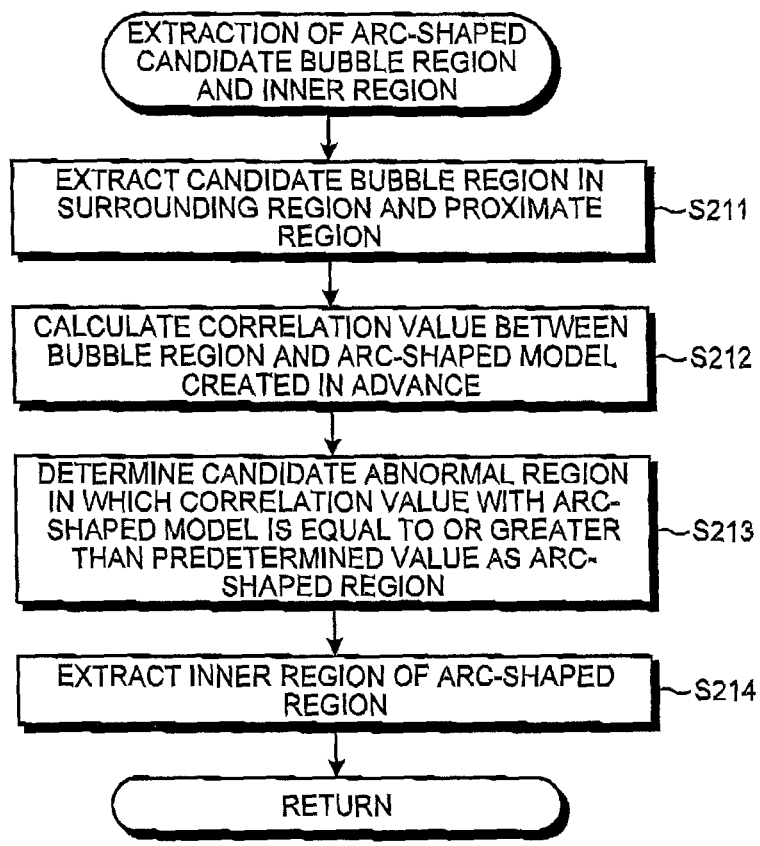
FIG. 13 is a flowchart illustrating a detailed process of extracting an arc-shaped candidate bubble region and an inner region.

FIG. 13 is a flowchart illustrating a detailed process of extracting an arc-shaped candidate bubble region and an arc-shaped inner region.

First, in step S211, the arc-shaped bubble region determining unit 232a extracts a candidate bubble region in the surrounding region A27 of the candidate abnormal region A20 and a region in the vicinity of the surrounding region A27. In the case of FIG. 12, the candidate bubble regions A22 to A24 and A26 are extracted from the candidate bubble regions A22 to A26 set in step S25. Subsequently, in step S212, the arc-shaped bubble region determining unit 232a calculates a correlation value between the extracted candidate bubble regions A22 to A24 and A26 and an arc-shaped model created in advance. In step S213, a candidate bubble region in which the correlation value with the arc-shaped model is equal to or greater than a predetermined threshold value is determined as an arc-shaped candidate bubble region. For example, in the case of FIG. 12, the candidate bubble regions A22 to A24 are determined as an arc-shaped candidate bubble region. Further, in step S214, the arc-shaped bubble region determining unit 232a extracts an inner region A28 of the candidate bubble regions A22 to A24 determined as an arc-shaped region. After that, the processing returns to the main routine.

In step S28, the arc-shaped inner region determining unit 232b determines whether the arc-shaped inner region A28 extracted in step S27 or the surrounding region A27 of the candidate abnormal region A20 is an inner region of an arc-shaped region.

When the surrounding region A27 of the candidate abnormal region A20 is an inner region of an arc-shaped region (Yes in step S28), the bubble inside determining unit 230 determines that the surrounding region A27 is inside a bubble region (step S29). In this case, in step S30, the abnormal region determining unit 240 determines that the candidate abnormal region A20 in the surrounding region A27 is not an abnormal region.

On the other hand, when the surrounding region A27 of the candidate abnormal region A20 is not an inner region of an arc-shaped region (No in step S28), the bubble inside determining unit 230 determines that the surrounding region A27 is not inside the bubble region (step S31). In this case, in step S32, the abnormal region determining unit 240 determines that the candidate abnormal region A20 in the surrounding region A27 is an abnormal region.

As described above, according to the second embodiment, first, a region in which the color feature data is smaller than a first criterion value is determined as an abnormal region. With respect to only a region in which the color feature data is between the first criterion value and the second criterion value and which is likely to be an abnormal region with low confidence, it is determined whether the region is an abnormal region using a bubble region. Therefore, it is possible to improve the efficiency of the computation process.

Third Embodiment

Next, a third embodiment of the invention will be explained.

Figure 14:
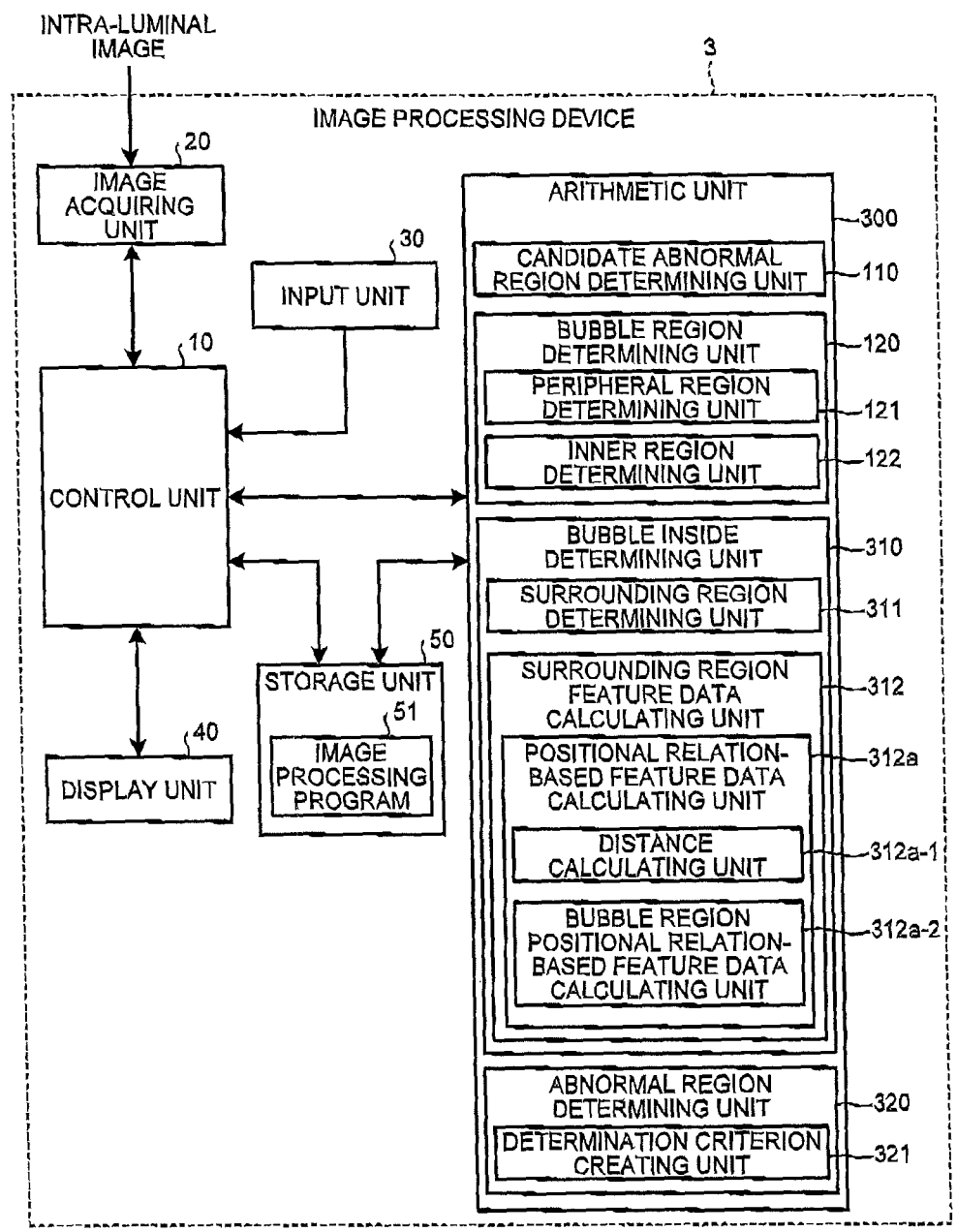
FIG. 14 is a block diagram illustrating the configuration of an image processing device according to a third embodiment of the invention.

FIG. 14 is a block diagram illustrating the configuration of an image processing device according to the third embodiment. As illustrated in FIG. 14, an image processing device 3 according to the third embodiment includes an arithmetic unit 300 which includes the candidate abnormal region determining unit 110, the bubble region determining unit 120, a bubble inside determining unit 310 that determines whether the candidate abnormal region is present inside the bubble region based on the determination result of the bubble region, and an abnormal region determining unit 320 that determines whether the candidate abnormal region is an abnormal region based on the determination result of the bubble inside determining unit 310. The configuration and the operation of the candidate abnormal region determining unit 110 and the bubble region determining unit 120 are the same as those described in the first embodiment. Moreover, the configuration of the image processing device 3 other than the arithmetic unit 300 is the same as that illustrated in FIG. 1.

The bubble inside determining unit 310 includes a surrounding region determining unit 311 that determines the surrounding region of the candidate abnormal region and a surrounding region feature data calculating unit 312 that calculates a feature data based on the surrounding region. The surrounding region feature data calculating unit 312 includes a positional relation-based feature data calculating unit 312a that calculates a feature data based on a positional relation of the bubble region in the surrounding region and the region in the vicinity of the surrounding region. The positional relation-based feature data calculating unit 312a includes a distance calculating unit 312a-1 that calculates the distance between bubble regions and a bubble region positional relation-based feature data calculating unit 312a-2 that calculates the feature data based on a positional relation between the arc-shaped region and the halation region.

The abnormal region determining unit 320 includes a determination criterion creating unit 321 that adaptively creates a determination criterion based on the information on the surrounding region of the candidate abnormal region.

Figure 15:
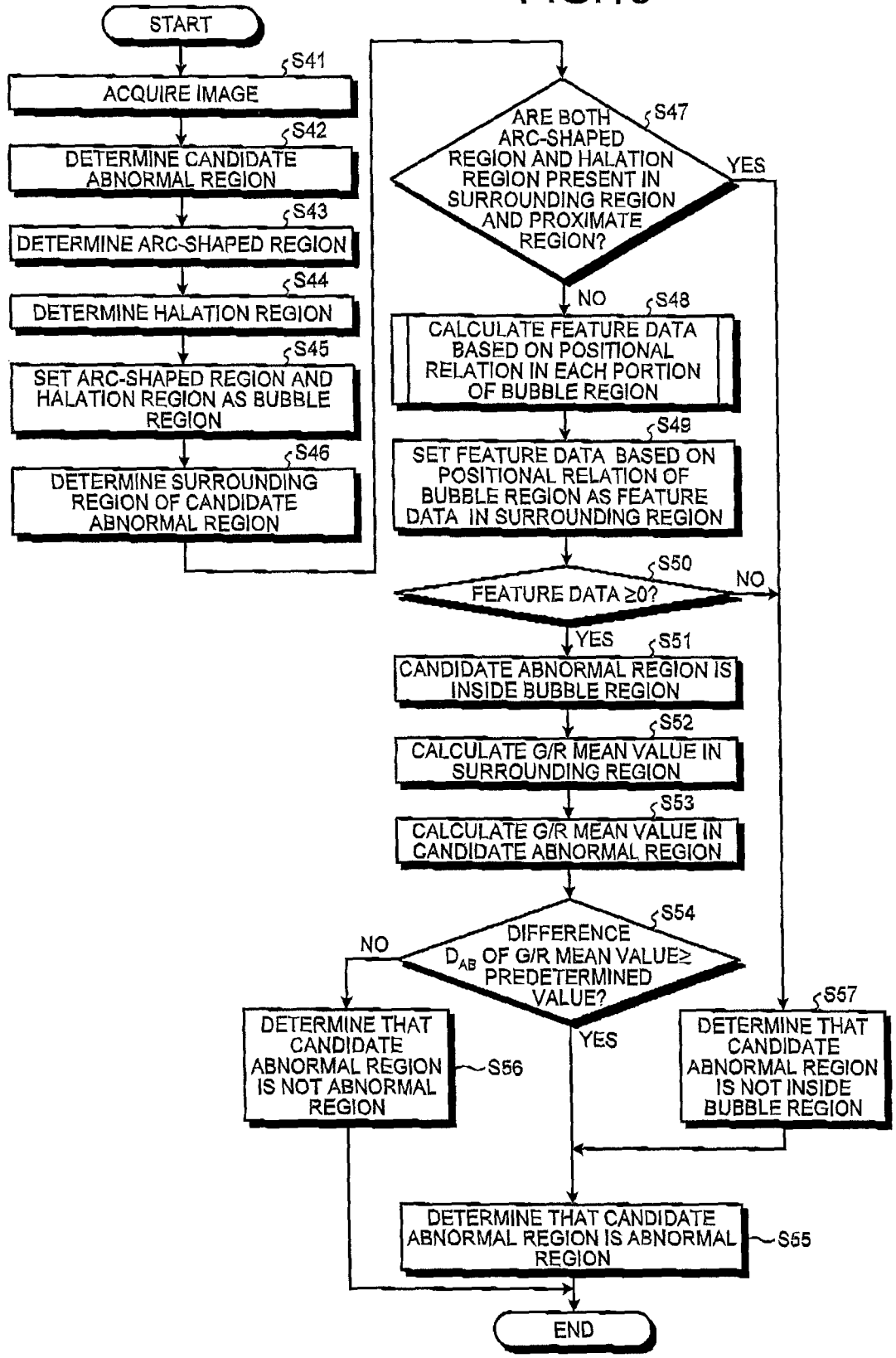
FIG. 15 is a flowchart illustrating the operation of the image processing device according to the third embodiment of the invention.

Next, the operation of the image processing device according to the third embodiment will be explained. FIG. 15 is a flowchart illustrating the operation of the image processing device according to the third embodiment.

Figure 16:
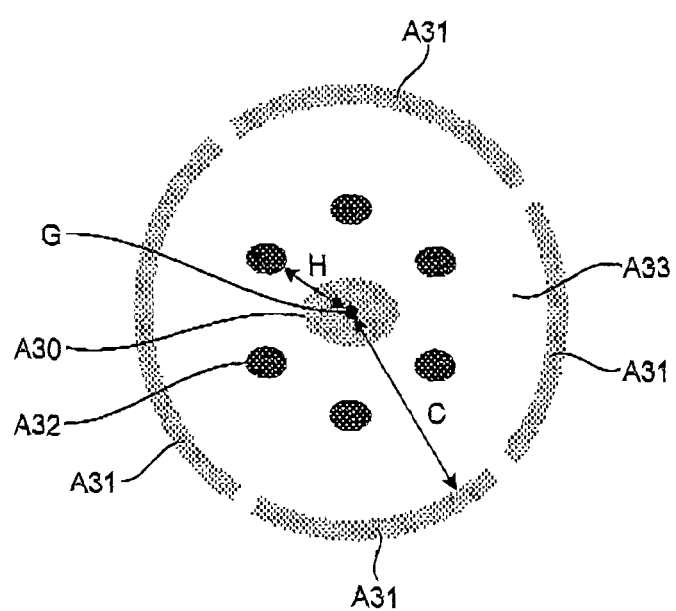
FIG. 16 is a schematic view explaining an image processing method according to the third embodiment.

In FIG. 15, the operations of steps S41 to S46 correspond to the operations of steps S01 to S06 illustrated in FIG. 2. FIG. 16 illustrates a candidate abnormal region A30, an arc-shaped region A31, a halation region A32, and a surrounding region A33 which are determined from the image in steps S41 to S46.

In step S47, the bubble region positional relation-based feature data calculating unit 312a-2 determines whether both the arc-shaped region A31 and the halation region A32 which constitute the bubble region are mixedly present in the surrounding region A33 and the region in the vicinity of the surrounding region A33. Here, in the bubble region, a halation is generally observed in the inner side of an arc-shaped region that constitutes a portion having an approximately circular shape (including a shape similar to a circle such as an ellipse). Thus, a region where both a portion determined as the arc-shaped region A31 and a portion determined as the halation region A32 are mixedly present can be determined not to be the bubble region.

When both the arc-shaped region A31 and the halation region A32 are not mixedly present in the surrounding region A33 and the region in the vicinity of the surrounding region A33 (No in step S47), the positional relation-based feature data calculating unit 312a calculates the feature data based on the positional relation in each portion of the bubble region (step S48).

Figure 17:
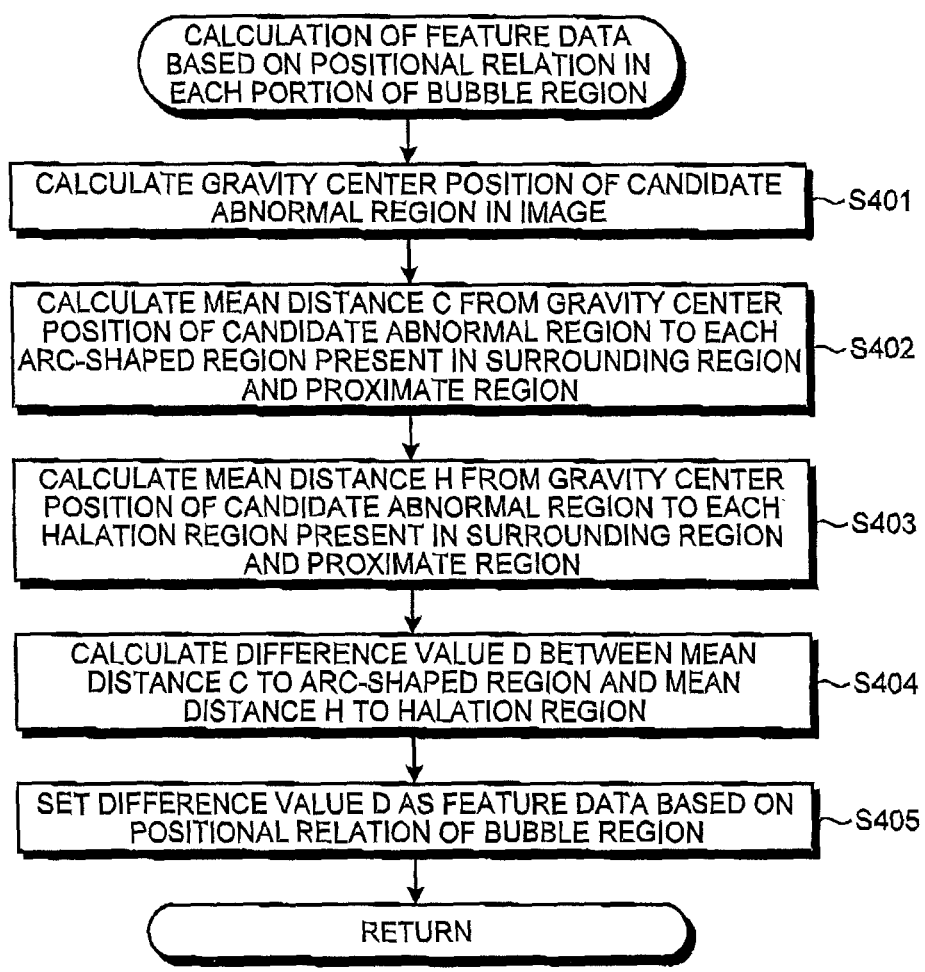
FIG. 17 is a flowchart illustrating a detailed process of calculating a feature data based on a positional relation at each position of a bubble region.

FIG. 17 is a flowchart illustrating a detailed process of calculating the feature data based on the positional relation in each portion of the bubble region. First, in step S401, the bubble region positional relation-based feature data calculating unit (hereinafter, simply referred to as a feature data calculating unit) 312a-2 calculates the gravity center position G of the candidate abnormal region A30 in the image. Subsequently, in step S402, the feature data calculating unit 312a-2 calculates the mean distance C from the gravity center position G of the candidate abnormal region A30 to the respective arc-shaped regions A31 present in the surrounding region A33 and the region in the vicinity of the surrounding region A33. Moreover, in step S403, the feature data calculating unit 312a-2 calculates a mean distance H from the gravity center position G of the candidate abnormal region A30 to the respective halation regions A32 present in the surrounding region A33 and the region in the vicinity of the surrounding region A33. Further, the feature data calculating unit 312a-2 calculates a difference D between the mean distance C to the arc-shaped region A31 and the mean distance H to the halation region A32 using the following equation (3) (step S404).

$$D = C - H \qquad (3)$$

In step S405, the positional relation-based feature data calculating unit 312a sets the difference D calculated in this way as a feature data based on the positional relation in each portion of the bubble region in the surrounding region A33 and the region in the vicinity of the surrounding region A33.

In step S49, the surrounding region feature data calculating unit 312 sets the feature data (the difference D) based on the positional relation in each portion of the bubble region as a feature data in the surrounding region A33.

In step S50, the bubble inside determining unit 310 determines whether the feature data (namely, the difference D) in the surrounding region A33 is equal to or greater than zero.

When the feature data in the surrounding region A33 is equal to or greater than zero (Yes in step S50), the bubble inside determining unit 310 determines that the candidate abnormal region 730 is inside the bubble region (step S51). This is because the fact that the difference D is equal to or greater than zero means that the halation region A32 can be determined to be present inside the arc-shaped region A31.

Subsequently, in step S52, the determination criterion creating unit 321 calculates the mean value (G/R mean value) of the G/R values in portions of the surrounding region A33 other than the candidate abnormal region A30 and the halation region A32.

In steps S53 to S55, the abnormal region determining unit 320 determines whether the candidate abnormal region A30 is an abnormal region using the G/R mean value calculated in step S52 as a determination criterion. Specifically, first, in step S53, the G/R mean value in the respective candidate abnormal regions A30 is calculated. Moreover, in step S54, it is determined whether a difference $D_{AB}$ between the G/R mean value in the surrounding region A33 and the G/R mean value in the candidate abnormal region A30 is equal to or greater than a predetermined threshold value (predetermined value). When the difference $D_{AB}$ is equal to or greater than the predetermined value (Yes in step S54), the abnormal region determining unit 320 determines that the candidate abnormal region A30 is an abnormal region (step S55). On the other hand, when the difference $D_{AB}$ is smaller than the predetermined value (No in step S54), the abnormal region determining unit 320 determines that the candidate abnormal region A30 is not an abnormal region (step S56).

Moreover, when it is determined in step S47 that both the arc-shaped region and the halation region are mixedly present in the surrounding region A33 and the region in the vicinity of the surrounding region A33 (Yes in step S47), the bubble inside determining unit 310 determines that the candidate abnormal region is not inside the bubble region (step S57). In this case, in step S55, the abnormal region determining unit 320 determines that the candidate abnormal region A30 is an abnormal region.

Moreover, even when the feature data D is smaller than zero (No in step S50), the bubble inside determining unit 310 determines that the candidate abnormal region is not inside the bubble region (step S57).

As described above, according to the third embodiment, since it is determined whether the surrounding region of the candidate abnormal region is present inside the bubble region based on the positional relation of the portions that constitute the bubble region, it is possible to improve the detection accuracy of the bubble region.

Third Modification Example

In the first to third embodiments described above, although the G/R value has been used as the color feature data which is used in determining the candidate abnormal region, various color feature dates such as the respective RGR values, relative values (B/G values or the like) of the respective RGB values, brightness and color difference calculated by YCbCr conversion, or hue, saturation, and lightness calculated by HSI conversion can be used. For example, when the B/G value is used as the color feature data, it is easy to determine a lesion of a region covered by the bile that is yellow. Here, B and G components of an illumination light that illuminates the lumen of a subject are absorbed in a red region by approximately the same amount. Thus, there is not a great difference between the B and G values in many regions of the lumen and a bleeding region. However, since the amount of absorption of the B component increases in the bile, the B value decreases in the bile region, and it becomes easy to detect a change in the G value. Thus, a region in the image in which the B/G value is equal to or greater than a predetermined value can be determined as a lesion, and a region in which the B/G value is smaller than the predetermined value can be determined as a region other than the lesion.

According to the first to third embodiments and the modification examples thereof, when the candidate abnormal region determined based on the first determination criterion is determined to be present inside the bubble region, it is determined whether the candidate abnormal region is an abnormal region using the second determination criterion different from the first determination criterion. Thus, it is possible to suppress a mucosal region inside bubbles from being erroneously detected as an abnormal region.

The image processing device according to the first to third embodiments and the modification examples thereof can be implemented by an image processing program recorded on a recording medium being executed by a computer system such as a personal computer or a workstation. Moreover, the computer system may be used in a state of being connected to an apparatus such as another computer system or a server via a local area network, a wide area network (LAN/WAN) or a public line such as the Internet. In this case, the image processing device according to the first to third embodiments may acquire image data of the intra-luminal images via these networks, output image processing results to various output apparatuses (a viewer, a printer, and the like) connected via these networks, and store the image processing results in a storage device (a recording medium, a reading device thereof, and the like) connected via these networks.

The invention is not limited to the first to third embodiments and the modification examples thereof, but various inventions can be formed by appropriately combining multiple constituent components disclosed in the respective embodiments and modification examples. For example, some constituent components may be removed from all constituent components illustrated in the respective embodiments and modification examples, and constituent components illustrated in other embodiments and modification examples may be appropriately combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device for an endoscope, comprising:
   a processor comprising hardware, the processor being configured to implement:
   a candidate abnormal region determining unit that calculates a color feature data by using pixel values of an intra-luminal image captured by the endoscope and determines a candidate abnormal region from the intra-luminal image by comparing the calculated color feature data with a first determination criterion;
   a bubble region detecting unit that detects a bubble region from the intra-luminal image, wherein the bubble region is a region on which a bubble comprising a body of gas within a liquid is captured in the intra-luminal image;
   a bubble inside determining unit that determines whether the candidate abnormal region is present inside the detected bubble region based on a detection result of the bubble region; and
   an abnormal region determining unit that determines whether the candidate abnormal region is an abnormal region using an amount of red in the calculated color feature data and a second determination criterion less inclusive with respect to the amount of red than the first determination criterion when the candidate abnormal region is determined to be present inside the detected bubble region;
   wherein portions in the intra-luminal image that are determined to be abnormal region by satisfying the second determination criterion are fewer than portions in the intra-luminal image that are determined to be the candidate abnormal region by satisfying the first determination criterion; and
   wherein the bubble region detecting unit detects, as the bubble region, a region having an arc-shaped region and a halation region from the intra-luminal image.

2. The image processing device according to claim 1, wherein the abnormal region determining unit includes a determination criterion switching unit that switches to the second determination criterion based on a determination result of the bubble inside determining unit.

3. The image processing device according to claim 1, wherein the abnormal region determining unit includes a determination criterion creating unit that adaptively creates the second determination criterion based on information on a surrounding region of the candidate abnormal region.

4. The image processing device according to claim 3, wherein portions in the intra-luminal image that are determined to be the abnormal region by satisfying the second determination criterion are fewer than portions in the intra-luminal image that are determined to be the abnormal region by satisfying the first determination criterion.

5. The image processing device according to claim 1, wherein the bubble region detecting unit includes a determination range determining unit that determines a determination range where the bubble region in the intra-luminal image is detected based on the determination result of the candidate abnormal region.

6. The image processing device according to claim 1, wherein the bubble region detecting unit includes a peripheral region determining unit that determines a region which has features of a peripheral region of the bubble region.

7. The image processing device according to claim 6, wherein the peripheral region determining unit includes an arc-shaped region determining unit that determines the arc-shaped region.

8. The image processing device according to claim 1, wherein the bubble region detecting unit includes an inner region determining unit that determines a region which has features of an inner region of the bubble region.

9. The image processing device according to claim 8, wherein the inner region determining unit includes a halation region determining unit that determines the halation region.

10. The image processing device according to claim 1, wherein
the bubble inside determining unit includes
a surrounding region determining unit that determines a surrounding region surrounding the candidate abnormal region, and
a surrounding region feature data calculating unit that calculates a surrounding region feature data that is a feature data of the surrounding region based on the detection result of the bubble region in the surrounding region and a region in the vicinity of a contour of the surrounding region among the detection results of the bubble region by the bubble region detecting unit.

11. The image processing device according to claim 10, wherein the surrounding region feature data calculating unit includes an area calculating unit that calculates the area of the bubble region in the surrounding region and the region in the vicinity of the surrounding region.

12. The image processing device according to claim 11, wherein the area calculating unit includes a contour extracting unit that extracts contour pixels of the surrounding region, calculates the area of the contour pixels, and calculates a normalized area of the area of the bubble region based on the area of the contour pixels.

13. The image processing device according to claim 10, wherein the surrounding region feature data calculating unit includes a positional relation-based feature data calculating unit that calculates a feature data based on a positional relation of multiple portions that configure the bubble region in the surrounding region and the region in the vicinity of the surrounding region.

14. The image processing device according to claim 13, wherein the positional relation-based feature data calculating unit includes a distance calculating unit that calculates the distance between the multiple portions in the surrounding region and the region in the vicinity of the surrounding region and the candidate abnormal region.

15. The image processing device according to claim 13, wherein the bubble region detecting unit includes
a peripheral region determining unit that determines a region which has the features of the peripheral region of the bubble region included in the multiple portions; and
an inner region determining unit that determines a region which has the features of the inner region of the bubble region included in the multiple portions, and
the positional relation-based feature data calculating unit includes a bubble region positional relation-based feature data calculating unit that calculates a feature data based on a positional relation between the region which has the features of the peripheral region and the region which has the features of the inner region.

16. The image processing device according to claim 1, wherein
the bubble inside determining unit includes
a surrounding region determining unit that determines a surrounding region of the candidate abnormal region; and
a surrounding region feature determining unit that determines the features of the bubble region in the surrounding region based on the detection result of the bubble region in the surrounding region and the region in the vicinity of the surrounding region among the detection results of the bubble region by the bubble region detecting unit.

17. The image processing device according to claim 16, wherein
the surrounding region feature determining unit includes
an arc-shaped bubble region determining unit that determines whether the bubble region in the surrounding region and the region in the vicinity of the surrounding region includes the arc-shaped region; and
an arc-shaped inner region determining unit that determines whether the surrounding region is an inner region of the arc-shaped region.

18. An image processing method for an endoscope using a processor and a memory storing computer readable instructions that, when executed by the processor, implement the steps comprising:
calculating a color feature data by using pixel values of an intra-luminal image captured by the endoscope and determining a candidate abnormal region from the intra-luminal image by comparing the calculated color feature data with a first determination criterion;
detecting a bubble region from the intra-luminal image, wherein the bubble region is a region on which a bubble comprising a body of gas within a liquid is captured in the intra-luminal image;
determining whether the candidate abnormal region is present inside the detected bubble region based on a detection result of the bubble region; and
determining whether the candidate abnormal region is an abnormal region using an amount of red in the calculated color feature data and a second determination criterion less inclusive with respect to the amount of red than the first determination criterion when the candidate abnormal region is determined to be present inside the detected bubble region;
wherein portions in the intra-luminal image that are determined to be the abnormal region by satisfying the second determination criterion are fewer than portions in the intra-luminal image that are determined to be the candidate abnormal region by satisfying the first determination criterion; and wherein the detecting the bubble region detects, as the bubble region, a region having an arc-shaped region and a halation region from the intra-luminal image.

19. A non-transitory computer readable storage device with an executable program stored thereon, wherein the program instructs a processor to perform for an endoscope:

calculating a color feature data by using pixel values of an intra-luminal image captured by the endoscope and determining a candidate abnormal region from the intra-luminal image by comparing the calculated color feature data with a first determination criterion;

detecting a bubble region from the intra-luminal image, wherein the bubble region is a region on which a bubble comprising a body of gas within a liquid is captured in the intra-luminal image;

determining whether the candidate abnormal region is present inside the detected bubble region based on a detection result of the bubble region; and determining whether the candidate abnormal region is an abnormal region using an amount of red in the calculated color feature data and a second determination criterion less inclusive with respect to the amount of red than the first determination criterion when the candidate abnormal region is determined to be present inside the detected bubble region;

wherein portions in the intra-luminal image that are determined to be the abnormal region by satisfying the second determination criterion are fewer than portions in the intra-luminal image that are determined to be the candidate abnormal region by satisfying the first determination criterion; and wherein the detecting the bubble region detects, as the bubble region, a region having an arc-shaped region and a halation region from the intra-luminal image.

* * * * *